United States Patent
Hoffmann et al.

(10) Patent No.: US 10,235,753 B2
(45) Date of Patent: Mar. 19, 2019

(54) AUTOMATIC RECOGNITION OF ANATOMICAL LANDMARKS

(71) Applicants: Matthias Hoffmann, Nürnberg (DE); Norbert Strobel, Forchheim (DE)

(72) Inventors: Matthias Hoffmann, Nürnberg (DE); Norbert Strobel, Forchheim (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 15/459,778

(22) Filed: Mar. 15, 2017

(65) Prior Publication Data
US 2017/0270663 A1 Sep. 21, 2017

(30) Foreign Application Priority Data

Mar. 15, 2016 (DE) .................. 10 2016 204 225

(51) Int. Cl.
*G06T 7/00* (2017.01)
*A61B 5/02* (2006.01)
(Continued)

(52) U.S. Cl.
CPC ........ *G06T 7/0012* (2013.01); *A61B 5/02007* (2013.01); *A61B 5/7271* (2013.01);
(Continued)

(58) Field of Classification Search
None
See application file for complete search history.

(56) References Cited

U.S. PATENT DOCUMENTS

| 2011/0142318 A1 | 6/2011 | Chen et al. | |
| 2011/0191283 A1* | 8/2011 | Voigt | G06N 5/00 706/54 |

(Continued)

FOREIGN PATENT DOCUMENTS

WO WO2015193055 A1 12/2015

OTHER PUBLICATIONS

Rettmann, M. E., et al. "Identification of left pulmonary vein ostia using centerline tracking." Medical Imaging 2009: Biomedical Applications in Molecular, Structural, and Functional Imaging. vol. 7262. International Society for Optics and Photonics, 2009.*

(Continued)

*Primary Examiner* — Vu Le
*Assistant Examiner* — Tracy Mangialaschi
(74) *Attorney, Agent, or Firm* — Lempia Summerfield Katz LLC

(57) ABSTRACT

A method for automatic recognition of at least one anatomical landmark in a hollow organ of a patient is provided. The method includes providing an image dataset of the hollow organ, establishing or providing a three-dimensional mesh of a surface of the hollow organ from the image dataset, and determining a centerline of the mesh by skeletization. At least one feature is determined for each of a plurality of points on the centerline. A classifier pre-trained on the at least one feature is used for detecting candidates for the at least one anatomical landmark from the plurality of points. The candidates are grouped together with a distance from one another below a threshold. At least one specification determined from the anatomy of the hollow organ is used for confirming or rejecting the candidates for the at least one anatomical landmark. One or more candidates are defined as an anatomical landmark.

16 Claims, 1 Drawing Sheet

(51) Int. Cl.
*A61B 5/00* (2006.01)
*G06T 17/20* (2006.01)
*G06T 7/73* (2017.01)

(52) U.S. Cl.
CPC ............... *A61B 5/742* (2013.01); *G06T 7/73* (2017.01); *G06T 17/20* (2013.01); *G06T 2207/30101* (2013.01); *G06T 2207/30172* (2013.01); *G06T 2210/41* (2013.01)

(56) References Cited

U.S. PATENT DOCUMENTS

| | | | |
|---|---|---|---|
| 2011/0224542 A1* | 9/2011 | Mittal | G06T 7/0016 600/425 |
| 2012/0071755 A1 | 3/2012 | Zheng et al. | |
| 2014/0003699 A1 | 1/2014 | Moulik | |
| 2014/0355854 A1 | 12/2014 | Kelm et al. | |
| 2015/0235360 A1 | 8/2015 | Zheng et al. | |

OTHER PUBLICATIONS

Telea, Alexandru, and Andrei Jalba. "Computing Curve Skeletons from Medial Surfaces of 3D Shapes." TPCG. 2012.*

Tobon-Gomez, Catalina, et al. "Benchmark for algorithms segmenting the left atrium from 3D CT and MRI datasets." IEEE transactions on medical imaging 34.7 (2015): 1460-1473. (Year: 2015).*

European Search Report for European Application No. 17161119.7-1906, dated Jul. 26, 2017.

Jajamovich, Guido H., et al. "Non-invasive indicators of pulmonary hypertension from pulmonary veins quantification in sickle cell disease." Biomedical Imaging (ISBI), 2012 9th IEEE International Symposium on. IEEE, 2012.

German Office Action for German Application No. 10 2016 204 225.4, dated Nov. 11, 2016, with English Translation.

Hoffmann et al., "Automatic detection of Ostia in the left atrium", Bildverarbeitung für die Medizin (BVM), Informatik Aktuell, Springer Verlag, 2016.

Koch et al., "Automatic planning of atrial fibrillation ablation lines using landmark-constrained nonrigid registration", Journal of Medical Imaging, 1(1), 2014, pp. 1-7; 2014.

Krizhevsky et al., "ImageNet classification with deep convolutional neural networks", Advances in Neural Information Processing Systems, p. 1097, 2012.

R. Karim et al., "Left Atrium Pulmonary Veins: Segmentation and Quantification for Planning Atrial Fibrillation Ablation", Proc. of SPIE, vol. 7261, Medical Imaging, 2009.

Rettmann et al., "Identification of the left pulmonary vein ostia using centerline tracking", Proc. SPIE., vol. 7262, 2009.

Telea et al., "Computing curve skeletons from medial surfaces of 3D shapes, Theory and Practice of Computer Graphics", The Eurographics Association, 2012.

Zheng et al. "Precise segmentation of the left atrium in C-arm CT volumens with applications to atrial fibrillation", Proc. IEEE Int. Symp. Biomed. Imaging, IEEE, p. 1421, 2012.

* cited by examiner

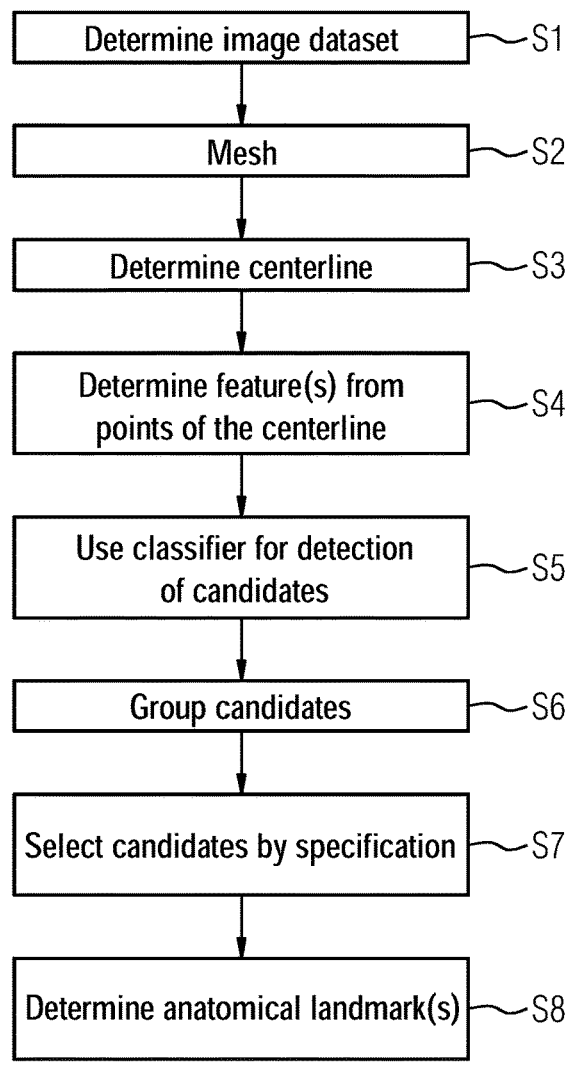
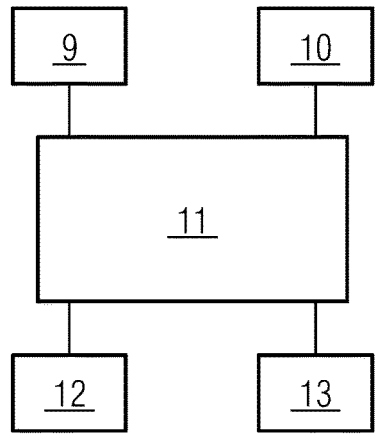

AUTOMATIC RECOGNITION OF ANATOMICAL LANDMARKS

This application claims the benefit of DE 10 2016 204 225.4, filed on Mar. 15, 2016, which is hereby incorporated by reference in its entirety.

BACKGROUND

The present embodiments relate to automatic recognition of at least one anatomical landmark in a hollow organ of a patient.

In general, a marking of anatomical landmarks in medical images is an important method of operation in order to prepare therapy planning, for example. One example from electrophysiology (EP) is the position of the pulmonary vein (PV) ostia and of the left atrial appendage (LAA) in a left atrium. The marking of the pulmonary vein ostia makes it easier to navigate catheters, since a position of the pulmonary vein ostia may be used for the automatic planning of catheter ablations (Koch et al., Automatic planning of atrial fibrillation ablation lines using landmark-constrained non-rigid registration, J. Med. Imag. 1(1), 2014), and since the form of the pulmonary vein ostia is an important criterion in relation to the choice of the cryo-balloon catheter to be used. A marking of the regions and a display in an x-ray overlay image is important for avoiding injuries caused by incorrect introduction of the catheter.

Other examples from EP are the detection of common ostia and the detection of the additional pulmonary veins (fifth PV). Other applications of the proposed method are found, for example, in the field of structural heart disease. In this field, the determination of diameters is important (e.g., for valve replacement, for the aorta valve), since the choice of size and possibly also type of valve may be made accordingly. The method may likewise be used for the detection of drainages. A further field of application is the field of abdominal aorta aneurysms (e.g., the choice of the appropriate stents). Additional applications are to be found in the detection of stenoses in blood vessels and airways as well as in the detection of fluctuations of the diameter (e.g., expansions and constrictions) in the gastro-intestinal tract.

For therapy planning, it is usual to mark important anatomical landmarks because anatomical landmarks are critical and may not be constricted under any circumstances (e.g., liver arteries in AAA therapies, coronary arteries in aorta valve positioning, LAA for EP ablation with atrial fibrillation) or because the anatomical landmarks are important for the positioning of devices (EP pulmonary vein isolation). In EP in general, the model of the left atrium is segmented using an automatic segmentation tool from a 3D CT or MRI volume. The 3D model (e.g., shown as a mesh) is then displayed to the observer in an interactive 3D view. The user marks a series of points on the surface of the mesh to create a marking of the PV ostium and of the LAA. Thereafter, the marked model is visualized as part of an x-ray overlay image, through which the x-ray overlay image may then be used to simplify the navigation within the 3D chamber.

As an alternative, a statistical model of the outline may be used for the segmentation, with the model containing the body of the LA and the pulmonary veins modeled individually in each case. On account of the structure of the model, the marking of the pulmonary vein ostia may be derived implicitly from the transition from LA body to the pulmonary veins (e.g., from the article by Karim et al., Left atrium pulmonary veins: segmentation and quantification for planning atrial fibrillation ablation, Proc. SPIE, 2009, p. 72611T ff. or from the article by Zheng et al., Precise segmentation of the left atrium in C-arm CT volumes with applications to atrial fibrillation, Proc. IEEE Int. Symp. Biomed. Imaging, IEEE, p. 1421 ff., 2012). As an alternative, a semi-automatic approach may also be used (Rettmann et al., Identification of the left pulmonary vein ostia using centerline tracking, Proc. SPIE., Vol. 7262, p. 726228ff., 2009). This method provides that the user clicks manually on each of the four pulmonary veins in order to calculate a centerline (e.g., three-dimensional (3D) central line). For each point of the centerline, the region of the intersection of the pulmonary veins will be calculated, and the first point, as from which the region of the intersection becomes significantly larger, will be considered as the ostium.

SUMMARY AND DESCRIPTION

The scope of the present invention is defined solely by the appended claims and is not affected to any degree by the statements within this summary.

The present embodiments may obviate one or more of the drawbacks or limitations in the related art. For example, recognition of an anatomical landmark in a hollow organ of a patient without any input from a user is provided.

The method for automatic recognition of at least one anatomical landmark in a hollow organ of a patient includes providing a medical image dataset of the hollow organ. A three-dimensional (3D) mesh of the surface of the hollow organ is established or provided from the image dataset. A centerline of the mesh is determined by skeletization. At least one feature is determined for each of a plurality of points on the centerline. A classifier pre-trained, for example, to the at least one feature is used for detecting candidates for the at least one anatomical landmark from the plurality of points. The candidates with a distance from one another below a pre-specified threshold are grouped together. At least one specification determined from the anatomy of the hollow organ is used for confirming or rejecting the candidates for the at least one anatomical landmark. One or more candidates are defined as an anatomical landmark. The advantages of the method of one or more of the present embodiments include the fact that intervention by a user is not needed, but all acts will be carried out automatically. Accordingly, a user-independent, consistent, very high quality, and improved accuracy in the recognition of anatomical landmarks may be achieved. This provides that the method is also very quick, so that a plurality of detections may be carried out in a very short time, and the clinical workflow may be speeded up. This is to the benefit of the patient. The method is also independent of the method of recording the 3D images, since the method does not work with volumes but with 3D meshes. For example, the method is suitable for recognizing at least one pulmonary vein ostium (e.g., all four or five or six pulmonary vein ostia) in a left atrium.

A centerline may be a 3D central line that has an elliptical diameter. The publication Telea et al., Computing curve skeletons from medial surfaces of 3D shapes, Theory and Practice of Computer Graphics, The Eurographics Association, 2012, discloses a method for computing such centerlines, for example. The lines are referred to herein as curve skeletons.

According to an embodiment, the feature may be formed by a minimum, maximum, or median of the cross-sectional surface of the centerline at the point and/or in its environment, spatially filtered minimum, spatially filtered maximum or spatially filtered median of the cross-sectional surface of the centerline at the point and/or in its environment, change of the diameter of the centerline, maximum diameter in the distal direction, minimum diameter in the proximal direction, position of the point in relation to the center of gravity of the hollow organ, direction of the centerline at the point, distance to the center of gravity of the hollow organ along the centerline, or curvature of the surface of the mesh along the cross-sectional surface of the centerline. A number of features or all of the features of the centerline may be determined. The features of the centerline may provide conclusions about the mesh and thus about the hollow organ in a simple manner. The determination of the features is described, inter alia, in the published document Hoffmann et al., Automatic detection of ostia in the left atrium, Bildverarbeitung für die Medizin (image processing for medicine) (BVM), Informatik Aktuell, Springer Verlag, 2016. All or specific points in the vicinity of branches of the centerline may be selected automatically, for example, as points for which the features will be determined. The feature or features may also be computed for all points on the centerline (e.g., the centerline may be completely scanned).

According to a further embodiment, a suggestion for treatment planning dependent on the anatomical landmark will be selected and output by a classifier. Such a suggestion for treatment planning may, for example, involve a suggestion for an apparatus to be introduced in the region of the anatomical landmark. Specifically, for example, in the case of a left atrium and a pulmonary vein ostium, a suggestion may be output for a catheter and/or a cryo-balloon or stent specifically adapted to the corresponding pulmonary vein ostium. For example, this makes the further procedure easier for a doctor, since the doctor now already has a suggestion supplied that the doctor may then assess in accordance with experience. The information about the catheters and cryo-balloons (e.g., size, brand) may be retrieved from a database.

A further classifier is used for recognition for each anatomical landmark to be recognized. Thus, when a number of landmarks are to be recognized, a specific classifier pre-trained in each case for the corresponding landmark will be used. This enables an especially high accuracy to be achieved in the recognition of the landmarks, since each classifier is specialized.

One classifier will be used for recognition for a number of anatomical landmarks. The method is greatly simplified by this and may be carried out especially quickly. The same classifier may also be used for anatomical landmarks and associated suggestion for a treatment plan.

According to a further embodiment, the classifier will be formed by a decision tree. Such classifiers are known, are readily available, are fast, and may be trained particularly well for the corresponding landmarks. For example, a support vector machine (SVM) or an artificial neuronal network may also be used for a classifier. The classifier or the classifiers is/are, for example, embodied as machine-learning. For training of the classifier or classifiers, for example, deep-learning methods may be used. Such methods are known, for example, from the article by Krizhevsky et al., ImageNet classification with deep convolutional neural networks, Advances in neural information processing systems, p. 1097 ff., 2012.

For carrying out the method in a simple manner, the three-dimensional mesh takes the form of a triangular mesh. This involves a widely-used and well-known form of the mesh, which is used in computer graphics and is frequently already present for three-dimensional medical datasets of hollow organs or may be easily created. Other forms (e.g., rectangular meshes) may also be used.

In accordance with a further embodiment, in the case of a left atrium, at least one specification, including both sides of the left atrium possessing a common ostium, each side of the atrium possessing two pulmonary vein ostia, the right side of the left atrium possessing two pulmonary vein ostia, each pulmonary vein possessing only one ostium, or any combination thereof, is used to confirm or reject candidates for anatomical landmarks from the pre-selection. The corresponding specifications will be applied accordingly to the candidates or to the already grouped candidates.

According to a further embodiment, the centerline is established such that a surface skeleton of the hollow organ is computed, and subsequently, a curve skeleton is formed form the surface skeleton. This is a known, simple method for determining centerlines (e.g., described in the publication Telea et al. (see above)).

The medical image dataset may be formed by computed tomography image data or from magnetic resonance tomography image data, for example.

For supporting the user or a doctor planning a therapeutic intervention, the determination is followed by a display of the anatomical landmarks on a display unit. The mesh positions that are linked to the anatomical landmarks of the centerline may also be computed.

One or more of the present embodiments also provide an apparatus for carrying out the method. The apparatus includes a processing unit (e.g., a processor) configured to provide a medical image dataset of the hollow organ, establish or provide a three-dimensional mesh of the surface of the hollow organ from the image dataset, and determine a centerline of the mesh by skeletization. The processor is also configured to determine at least one feature from a plurality of points on the centerline, apply a classifier pre-trained on the at least one feature for detecting candidates for the at least one anatomical landmark from the plurality of points, and collect the candidates with a distance from one another below a pre-specified threshold. The processor is further configured to use at least one specification determined from the anatomy of the hollow organ for confirming or rejecting the candidates for the at least one anatomical landmark, and determine one or more candidates as anatomical landmark by the classifier. The apparatus also includes a memory unit for storage of data, a communication unit for communication with a database, an input unit for input of user data, and a display unit for display of image data.

BRIEF DESCRIPTION OF THE DRAWINGS

FIG. 1 shows a flowchart of one embodiment of a method; and

FIG. 2 shows one embodiment of an apparatus configured to carry out the method.

DETAILED DESCRIPTION

FIG. 1 shows a flowchart of one embodiment of a method with eight acts S1 to S8. The method referring to a left atrium is shown as an example for a hollow organ, where the aim is to recognize pulmonary vein ostia (e.g., five: two left and three right). In act S1, a medical three-dimensional (3D) image dataset of a left atrium of a patient is provided (e.g., retrieved from a database or a storage medium or retrieved directly after the corresponding acquisition and made available). Such a three-dimensional medical image dataset may, for example, involve a computed tomography image dataset or a magnetic resonance tomography image dataset. In act S2, a 3D mesh (e.g., a triangle mesh) of the surface of the volume is computed from the image dataset. The mesh may also have been created beforehand, and now, merely is to be retrieved from a database or a storage medium and be made available, for example. Such a mesh generally has nodes and edges.

In act S3 a centerline (e.g., a 3D central line), which generally has an elliptical diameter, will be determined from the three-dimensional mesh. Such a determination of a centerline will generally be carried out by a skeletization. A suitable method is described, for example, in the article by Telea et al. (see further above), where a two-stage approach has been selected: a surface skeleton of the left atrium (LA) is computed, and subsequently, a curve skeleton is formed from the surface skeleton. The surface skeleton involves a two-dimensional (2D) manifold constructed from all the points that are the center of spheres plotted through the mesh. The characteristic of the mesh is re-established, and a gradient field is implicitly defined on the surface skeleton. The points on the surface skeleton are moved iteratively along the gradient field until the points converge along the singularities of the gradient field, which form the curve skeleton. The result is a shrunken mesh.

Subsequently, in a fourth act S4, at least one feature for each of a plurality of points on the centerline is determined. In one embodiment, the feature is formed by a minimum, maximum or median of the cross-sectional surface of the centerline at the point and/or its environment, spatially filtered minimum, spatially filtered maximum or spatially filtered median of the cross-sectional surface of the centerline at the point and/or its environment, change of the diameter of the centerline, maximum diameter in the distal direction, minimum diameter in the proximal direction, position of the point in relation to the center of gravity of the hollow organ, direction of the centerline at the point, distance to the center of gravity of the hollow organ along the centerline, or curvature of the surface of the mesh along the cross-sectional surface of the centerline. A number of points or all the points of the centerline may be determined. Points in the vicinity of branches of the centerline may be selected automatically, for example, as points for which the features will be determined. The feature or features may also be computed for all points on the centerline (e.g., the centerline may be completely scanned).

The radius or diameter of the pulmonary veins may be determined, for example. Generally, this is elliptical. The cross-sectional surface may be determined at the point and the normal vector. Subsequently, the intersection of the pulmonary veins with this cross-sectional surface may be determined. Then, the median of the distance from the point to the points of the pulmonary veins produced therefrom may be determined. Thereafter, a spatial median filtering on the radii along the pulmonary veins may be applied. Since the pulmonary vein ostium is characterized by the radius/diameter increasing in the direction of the center of the left atrium, the radii or diameters of the environment of the points will be used. To estimate the increase, the derivations of the radius/diameter may also be used. In order to provide that a strong increase at a point is not to be attributed to a local minimum in the diameter of the pulmonary veins, the maximum radius/diameter in the distal direction may also be determined. In order to provide that the pulmonary vein ostium will not be confused with a local expansion, the minimum radius/diameter in the proximal direction may also be determined. In addition, the normal vector and the distance to the center of the left atrium may be used.

In act S5, at least one classifier pre-trained on the at least one feature may be used for detecting candidates for the at least one anatomical landmark from the plurality of points. The classifier may, for example, involve a decision tree. It is sensible to pre-train the classifier or the classifiers based on a largest possible number of examples, so that the classifier delivers as accurate a result as possible. The training may be carried out, for example, by deep-learning methods. There may be provision, for recognition of a number of pulmonary vein ostia, for the respective ostium of each individual PV (e.g., left upper, left lower, right upper, right lower, common and additional PV) for using an individual classifier, but just one single classifier may also be used for a number of pulmonary vein ostia.

In addition, a corresponding suggestion may be established for a therapy plan from the same classifier or an individual classifier in this context for each candidate for the landmark (e.g., based on the anatomical circumstances). An example for establishing candidates for pulmonary vein ostia in this context may be a suggestion for the type/size and/or the type of a catheter or of a cryo-balloon to be used. Suggestions for stents and other medical equipment may also be included. This optional step is not shown in FIG. 1.

In act S6, candidates established by the classifier or the classifiers may be grouped together (e.g., clustered). This may be carried out, for example, such that candidates with a distance from one another below a previously defined threshold will be clustered together.

In act S7, at least one specification determined from the anatomy of the LA for confirming or rejecting candidates for the pulmonary vein ostia is used. Such specifications may state, for example, that only one single ostium is possible for each pulmonary vein or that a specific side of the LA has two ostia or three ostia (e.g., right side) or that both sides have a common ostium.

In act S8, in relation to the remaining candidates or clusters of candidates, one or more candidates or clusters are defined as the pulmonary vein ostium/ostia from the classifier or the classifiers, for example. For example, the largest cluster of candidates on the right side of the LA is defined as the first right pulmonary vein ostium, and the largest cluster of candidates on the left side is defined as first left pulmonary vein ostium. The second largest cluster is then the second left pulmonary vein ostium and the second right pulmonary vein ostium, respectively. If there is still an ostium on the right side of the LA, the ostium of the appendage (LAA) is involved.

Subsequently (not shown in FIG. 1), the result of the method (e.g., the pulmonary vein ostia established) will be displayed to a user or a doctor on a display unit. In addition (also not shown in FIG. 1), the corresponding suggestions for therapy plans or suggestion for therapy tools or devices to be used (e.g., type of catheter and cryo-balloon) may be displayed.

A visualization of the anatomical landmarks with live images from medical imaging apparatuses may subsequently be carried out. Thus, for example, live fluoroscopy images through the triangle mesh and the anatomical landmarks (e.g., left atrium with pulmonary vein ostia) may be displayed overlaid.

An apparatus for carrying out the method is shown in FIG. 2. The apparatus includes a processing unit 11 (e.g., a processor) connected to a communication unit 9, a memory unit 10, a display unit 12, and an input unit 13.

The present embodiments describe an automatic method for detecting anatomical marker points that may also be used for supporting therapy planning (e.g., by suggestions for selection of corresponding equipment and its positioning. The atrium may be represented as a triangle mesh, providing that the method is independent of the modality with which the medical image dataset has been recorded and also independent of the segmentation tool.

One or more of the present embodiments may be briefly summarized in the following way. For a fast and effortless support of a user, a method for automatic recognition of at least one anatomical landmark in a hollow organ of a patient is provided. The method includes: providing a medical image dataset of the hollow organ; establishing or providing a three-dimensional mesh of the hollow organ from the image dataset; determining a centerline of the mesh by skeletization; determining at least one feature of a plurality of points on the centerline; using a classifier pre-trained, for example, to the at least one feature for detecting candidates for the at least one anatomical landmark from the plurality of points; grouping together the candidates with a distance from one another below a pre-specified threshold; using at least one specification determined from the anatomy of the hollow organ for confirming or rejecting the candidates for the at least one anatomical landmark; and defining one or more candidates as an anatomical landmark (e.g., by the classifier).

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for automatic recognition of at least one anatomical landmark in a hollow organ of a patient, the method comprising:
providing a medical image dataset of the hollow organ;
establishing or providing a three-dimensional (3D) mesh of a surface of the hollow organ from the medical image dataset;
determining a centerline of the mesh by skeletization;
determining at least one feature for each of a plurality of points on the centerline;
detecting candidates for the at least one anatomical landmark from the plurality of points, the detecting comprising using a classifier pre-trained on the at least one feature;
grouping together the candidates with a distance from one another below a pre-specified threshold;
confirming or rejecting the candidates for the at least one anatomical landmark, the confirming or rejecting comprising using at least one specification determined from the anatomy of the hollow organ; and
defining one or more candidates as an anatomical landmark.

2. The method of claim 1, wherein the at least one feature is formed by a feature from the group consisting of: minimum, maximum or median of a cross-sectional surface associated with the centerline at the point, in an environment, or at the point and in the environment, spatially filtered minimum, spatially filtered maximum or spatially filtered median of the cross-sectional surface associated with the centerline at the point, in the environment or at the point and in the environment, change of a diameter associated with the centerline, maximum diameter in a distal direction, minimum diameter in a proximal direction, position of the point in relation to the center of gravity of the hollow organ, direction of the centerline at the point, distance to the center of gravity of the hollow organ along the centerline, and curvature of the surface of the mesh along the cross-sectional surface associated with the centerline.

3. The method of claim 1, further comprising selecting and outputting a suggestion dependent on the at least one anatomical landmark for treatment planning using a classifier.

4. The method of claim 1, wherein the hollow organ is formed by a left atrium, and the at least one anatomical landmark is formed by a pulmonary vein ostium.

5. The method of claim 3, wherein a number of pulmonary vein ostia are recognized.

6. The method of claim 1, wherein a further classifier is used for recognition for each anatomical landmark to be recognized.

7. The method of claim 1, wherein one classifier is used for recognition for a number of anatomical landmarks.

8. The method of claim 1, wherein the classifier is formed by a decision tree.

9. The method of claim 1, wherein the 3D mesh has the form of a triangle mesh.

10. The method of claim 4, wherein the at least one specification includes both sides of the left atrium possessing a common ostium, each side of the left atrium possessing two pulmonary vein ostia, a right side of the left atrium possessing two pulmonary vein ostia, each pulmonary vein possessing only one ostium, or any combination thereof.

11. The method of claim 1, wherein the centerline is established such that a surface skeleton of the hollow organ is computed and subsequently, a curve skeleton is formed from the surface skeleton.

12. The method of claim 1, wherein providing the medical image dataset of the hollow organ comprises forming the medical image dataset from computed tomography image data or from magnetic resonance tomography image data.

13. The method of claim 1, wherein the classifier is configured as machine-learning.

14. The method of claim 1, further comprising displaying the at least one anatomical landmark on a display unit after the defining of the one or more candidates as an anatomical landmark.

15. The method of claim 1, further comprising computing mesh positions that are linked to anatomical landmarks of the centerline.

16. An apparatus for automatic recognition of at least one anatomical landmark in a hollow organ of a patient, the apparatus comprising:
a processor configured to:
provide a medical image dataset of the hollow organ;
establish or provide a three-dimensional (3D) mesh of a surface of the hollow organ from the medical image dataset;

determine the centerline of the mesh, the determination of the centerline of the mesh comprising skeletization;

determine at least one feature for each of a plurality of points on the centerline;

detect candidates for the at least one anatomical landmark from the plurality of points, the detection of the candidates for the at least one anatomical landmark comprising application of a classifier pre-trained on the at least one feature;

group together the candidates with a distance from one another below a pre-specified threshold;

confirm or reject of the candidates for the at least one anatomical landmark, the confirmation or the rejection of the candidates comprising use of at least one specification determined from the anatomy of the hollow organ; and determine one or more candidates as an anatomical landmark through the classifier;

a memory configured to store the medical image dataset;

a communication unit configured to communicate with a database;

an input device configured for input of user data; and a display configured to display a representation of the medical image dataset.

\* \* \* \* \*